(12) United States Patent
Bruno et al.

(10) Patent No.: US 8,030,432 B2
(45) Date of Patent: Oct. 4, 2011

(54) COPOLYMERIZATION OF HYDROXYTYROSOL WITH FLAVONOIDS MEDIATED BY HORSERADISH PEROXIDASES

(75) Inventors: Ferdinando F. Bruno, Andover, MA (US); Nicole Favreau, Waltham, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 12/634,971

(22) Filed: Dec. 10, 2009

(65) Prior Publication Data

US 2011/0144298 A1   Jun. 16, 2011

(51) Int. Cl.
*C08G 63/02*   (2006.01)
*C08G 64/00*   (2006.01)

(52) U.S. Cl. .......................................... 528/219; 435/125
(58) Field of Classification Search .................. 435/125; 528/219

See application file for complete search history.

(56) References Cited

U.S. PATENT DOCUMENTS

| 7,098,246 B2 | 8/2006 | Geelings et al. |
| 7,273,951 B2 | 9/2007 | Biessen et al. |
| 2009/0035440 A1 | 2/2009 | Velikov |
| 2009/0215881 A1 | 8/2009 | Delaire et al. |

*Primary Examiner* — Terressa Boykin
(74) *Attorney, Agent, or Firm* — Roger C. Phillips

(57) ABSTRACT

The present invention provides a method of producing a copolymer of hydroxytyrosol, or its derivative, and at least one flavonoid comprising reacting hydroxytyrosol monomers or derivative with at least one flavonoid in the presence of an enzyme and hydrogen peroxide in an aqueous solution.

9 Claims, 2 Drawing Sheets

COPOLYMERIZATION OF HYDROXYTYROSOL WITH FLAVONOIDS MEDIATED BY HORSERADISH PEROXIDASES

BACKGROUND OF THE INVENTION

1. Field of the Invention

The present invention relates generally to an enzymatic mediated copolymerization process of hydroxytyrosol with different flavonoids which results in a novel polymer of polyphenol. This polymer has improved electrical and optical properties, water solubility, and consequently processability (compared to phenolic resins) and may be synthesized using chemically safe and environmentally friendly conditions for the formation of antioxidant for foods or anticancer drugs.

2. Description of the Related Art

Naturally occurring flavonoids have attracted a great deal of attention in the last decade primarily due to their potent antioxidant activity. In particular, compounds like catechins belonging to the flavonoid family have been found to possess very good antioxidant activity. These flavonoids are naturally occurring and are found in green and white teas, cocoa, red wine, strawberries, cherries, peaches, apples, plums, beans and lentils. Common catechins are: (+)-catechin, (−)-catechin, (−)-epicatechin, epicatechin gallate (ECG), and epigallocatechin-3-gallate (EGCG). In a recent study, the addition of 300 mg/Kg catechin showed inhibition of oxidation in red meat and poultry.

Moreover, catechins were found more effective against lipid oxidation in raw pork compared to BHA and BHT. However, the commercial use of catechins as antioxidants has been impeded by their poor thermal stability. Flavonoids like EGCG are known to decompose at room temperature after a few minutes. Curcumin decomposes at room temperature in aqueous solution. Other flavonoids, like epicatechins, decompose at temperatures beyond 45° C. One objective is to overcome the limitations of the naturally occurring flavonoids to render them more stable through polymerization. To accomplish this, we propose a unique and simple one-pot synthesis to make copolymeric flavonoids that exhibit enhanced stability and activity over the naturally occurring forms. This novel approach will involve the use of flavonoids, isolated from naturally occurring materials that will be polymerized using oxidoreductases such as horseradish peroxidase (HRP).

Enzymatic polymerization of phenol in aqueous solutions was initially investigated as a possible benign and environmentally friendly solution to the synthesis of polyphenols (J. A. Akkara, K. J. Senecal, and D. L. Kaplan, *Jour. of Pol. Part A: Pol. Chem.*, 29, 1561, (1991)).

These initial attempts were unsuccessful as only very low molecular weight oligomers could be formed which had limited properties to meet the requirements for such applications. Alternative enzymatic reactions have since been investigated to improve molecular weight and the mechanical, thermal, optical and electronic properties of these polymers including micelles, air-water interface monolayers and mixture into various organic solvents. Although the molecular weights and properties of these polyphenols were improved, their commercial application remains limited due to extensive branching and poor solubility and processability of the resulting polymers (Madhu S. Ayyagari, Kenneth A. Marx, Sukant K. Tripathy, Joseph A. Akkara, and David L. Kaplan: "Controlled Free-Radical Polymerization of Phenol Derivatives by Enzyme-Catalyzed Reactions in Organic Solvents" *Macromolecules* 1995, 28, 5192).

SUMMARY OF THE INVENTION

The approach described in this invention addresses these problematic issues and results in a new class of copolymers which are prepared in aqueous medium using an environmentally safe, and facile "one-step" reaction. In addition, these copolymers are water soluble with improved properties including molecular weight, structural, thermal, mechanical, electronic and optical and processability than current art synthetic routes. In the present invention, enzymatic copolymerization of hydroxytyrosol (HDT) monomer with at least one flavonoid, and more preferably quercetin (QUE), epicatechin (EPI), and rutin (RUT) was optimized by carrying out the reaction in the presence of the enzyme horseradish peroxidases (HRP). It is demonstrated in this invention that a new class of polyphenols may be designed, synthesized and tuned, based on the type and position of functionalization of the monomer. The ease of synthesis and processability of this approach described in this invention will afford extensive opportunities of these new polyphenols in a wide variety of industrial, medical, electronic, food and optical applications.

It is an objective of the present invention to provide a novel approach for the synthesis of a water soluble processable copolyphenol with improved properties.

It is yet another objective of the present invention to provide an approach as described above which results in the production of a polyHDT-co-QUE which has enhanced water solublility, electronic and optical properties over natural polyflavonoids and polyphenols prepared using prior art aqueous enzymatic synthetic routes.

It is yet another objective of the present invention to provide an approach as described above which results in the production of a water soluble form of a polyHDT-co-QUE which provides a synthetic route that may be carried out under neutral or near neutral pH conditions without the use of any other toxic reagents.

It is yet another objective of the present invention to provide a simple (one step), environmentally safe and chemically mild synthetic route over prior art for the synthesis of a water soluble and processable polyflavonoids and polyphenols containing HDT. Polymerization of flavonoids is generally disclosed by Bruno et al. in U.S. Patent Publication No. 2009/0170928, the disclosure of which is hereby incorporated by reference. However, polymerization of HDT with flavonoids is not disclosed in this U.S. Patent Publication.

It is yet another objective of the present invention to provide an approach as described above which results in environmentally safe processing of these polyHDT-co-QUE into various architectures including but not limited to gels, coatings, paints, micelles, reversed micelles, thin films, fibers, chaff materials, electrostatic sprays, food antioxidant anticancer drugs and membranes.

It is yet another objective of the present invention to provide an approach as described above which results in the synthesis of a polyHDT-co-QUE which may be used for applications including but not limited to wood composites laminates, foundry resins, abrasives, friction and molding materials, coatings and adhesives, fiber bonders and flame retardants light weight rechargeable batteries, rechargeable batteries, smart windows, chaff materials, and drug delivery systems.

It is yet another objective of the present invention to provide an approach as described above which results in the production of a polyHDT-co-EPI which has enhanced water solubility, electronic and optical properties over natural polyflavonoids and polyphenols prepared using prior art aqueous enzymatic synthetic routes.

It is yet another objective of the present invention to provide an approach as described above which results in the production of a water soluble form of a polyHDT-co-EPI which provides a synthetic route that may be carried out under neutral or near neutral pH conditions without the use of any other toxic reagents.

It is yet another objective of the present invention to provide an approach as described above which results in environmentally safe processing of these polyHDT-co-EPI into various architectures including but not limited to gels, coatings, paints, micelles, reversed micelles, thin films, fibers, chaff materials, electrostatic sprays, food antioxidant anticancer drugs and membranes.

It is yet another objective of the present invention to provide an approach as described above which results in the synthesis of a polyHDT-co-EPI which may be used for applications including but not limited to wood composites laminates, foundry resins, abrasives, friction and molding materials, coatings and adhesives, fiber bonders and flame retardants light weight rechargeable batteries, rechargeable batteries, smart windows, chaff materials, and drug delivery systems.

It is yet another objective of the present invention to provide an approach as described above which results in the production of a polyHDT-co-RUT which has enhanced water solublility, electronic and optical properties over natural polyflavonoids and polyphenols prepared using prior art aqueous enzymatic synthetic routes.

It is yet another objective of the present invention to provide an approach as described above which results in the production of a water soluble form of a polyHDT-co-RUT which provides a synthetic route that may be carried out under neutral or near neutral pH conditions without the use of any other toxic reagents.

It is yet another objective of the present invention to provide an approach as described above which results in environmentally safe processing of these polyHDT-co-RUT into various architectures including but not limited to gels, coatings, paints, micelles, reversed micelles, thin films, fibers, chaff materials, electrostatic sprays, food antioxidant anticancer drugs and membranes.

It is yet another objective of the present invention to provide an approach as described above which results in the synthesis of a polyHDT-co-RUT which may be used for applications including but not limited to wood composites laminates, foundry resins, abrasives, friction and molding materials, coatings and adhesives, fiber bonders and flame retardants light weight rechargeable batteries, rechargeable batteries, smart windows, chaff materials, and drug delivery systems.

Additional objectives, as well as features and advantages of the present invention, will be set forth in part in the description which follows, and in part will be obvious from the description or may be learned by practice of the invention. The objects, features and advantages of the present invention may be realized and attained by means of the instrumentalities and combinations particularly pointed out in the appended claims.

DETAILED DESCRIPTION OF THE PRESENTLY PREFERRED EMBODIMENTS

Accordingly, to achieve the foregoing objects and in accordance with the purpose of the present invention, as embodied and described herein, a method is provided for an enzymatic mediated copolymerization of hydroxytyrosol or its derivatives and at least one flavonoid in a mixed solution comprising an enzyme, hydrogen peroxide, and an aqueous solvent.

The derivative of hydroxytyrosol may have functional groups at the ortho and meta positions to sterically control the orientation of the monomers with respect to other monomers during the polymerization. Functional groups could include but are not limited to methoxy, methyl, ethyl, sulfonate, carboxylate and hydroxyl groups. These groups may be present in the ortho position of the monomer or comonomer. The flavonoid may be, but are not limited to, quercitin, catechin, epicatechin, or rutin, Kaempferol, Myricetin, Delphinidin, Cyananidin, Petunidin, Pelargonidin, Malvidin, epigallocatechin gallate, flavonone, Isoflavone, Chalcone, Anthocyanidin, Chrysin, Primuletin, Fisetin, Naringin, Hesperidin, Prunin, Daidzein, Genistein, Pelargonidin, cyaniding, etc.

The enzyme used for the copolymerization is preferably horse radish peroxidase, laccase or pegylated hemadine. The step of reacting hydroxytyrosol monomers with the flavonoid is preferably conducted at a temperature of 5 to 37 C. The amount of enzyme is preferably 0.4 to 2 mg/mL of the mixed solution. The amount of hydrogen peroxide is preferably 0.1 to 3% per volume of the mixed solution. The pH of the mixed solution is preferably 4.3 to 8.5, more preferably 6.0 to 8.5. The aqueous solvent preferably comprises ethanol and water.

One embodiment of the present invention provides a copolymerization of HDT and QUE comprising the preparation of an aqueous solution containing a HDT and QUE, an oxidizing agent which is comprised of an enzyme (horseradish peroxidase) and an electron acceptor (hydrogen peroxide). The procedure is a one-step, in situ reaction, which is highly selective and which produces minimal by-products and chemical waste. The resulting copolymer solution can be immediately used as is or purified via such techniques as dialysis, centrifuging and precipitation and then used for subsequent processing strategies.

Figure 1:
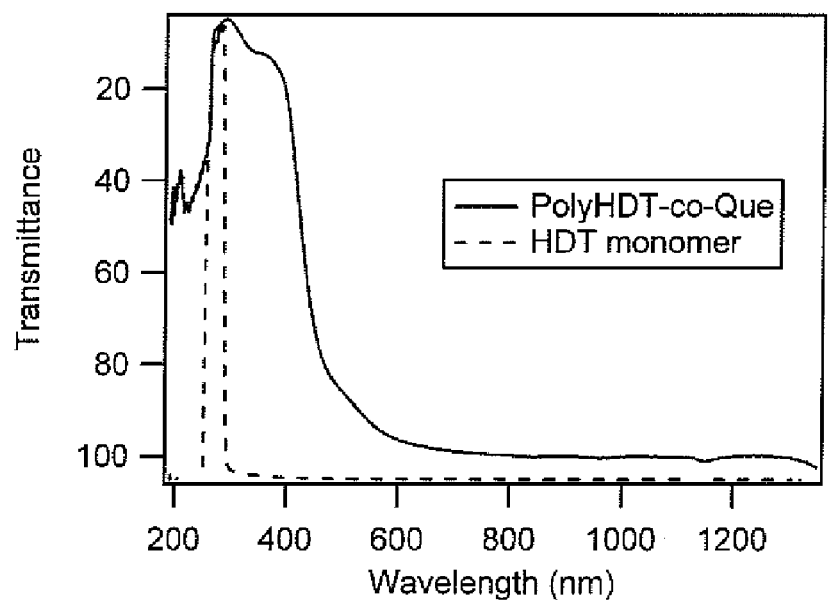
FIG. 1 shows the UV-Vis absorption spectra of the polyHDT-co-QUE formed in presence of HRP and of the monomer HDT.

FIG. 1 shows a comparison of the visible absorption spectra of the copolymerized HDT-co-QUE prepared with HRP and of the monomer HDT. As shown in this figure, strong, broad absorption well out into the visible is observed for the polymerized sample. This absorption is indicative of extended conjugation found in the copolyphenol.

Since copolyflavonoids prepared using prior art enzymatic strategies are difficult to process without using harsh, chemical modification or involved synthetic strategies, this new approach provides significant improvement in environmental compatibility, mild synthetic conditions, and environmentally safe processing opportunities for commercial application, such as in the food field.

Another embodiment of the present invention provides a method for an enzymatic mediated copolymerization of phenol substitute such as HDT and EPI comprising the preparation of an aqueous solution containing a HDT and EPI, and an oxidizing agent which is comprised of an enzyme (horseradish peroxidase) and an electron acceptor (hydrogen peroxide). The procedure is a one-step, in situ reaction, which is highly selective and which produces minimal by-products and chemical waste.

The resulting copolymer solution can be immediately used as is or purified via such techniques as dialysis, centrifuging and precipitation and then used for subsequent processing strategies.

Figure 2:
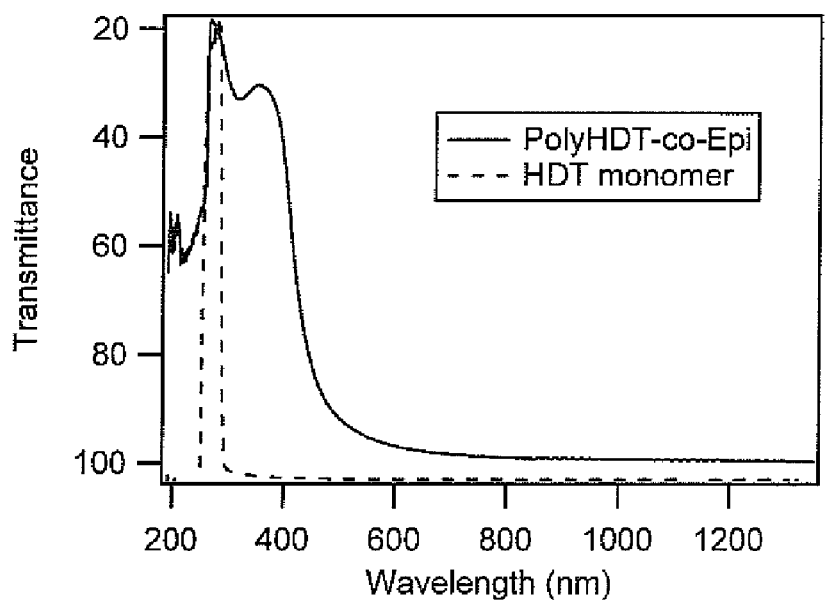
FIG. 2. UV-vis absorption spectra of the polyHDT-co-EPI formed in presence of HRP and of the monomer HDT.

FIG. 2 of this invention shows a comparison of the visible absorption spectra of the copolymerized HDT-co-EPI prepared with HRP. As shown in this figure, strong, broad absorption well out into the visible is observed for the polymerized sample. This absorption is indicative of extended conjugation found in the copolyphenol.

Still another embodiment of the present invention provides a method for an enzymatic mediated copolymerization of phenol substitute such as HDT and RUT comprising the preparation of an aqueous solution containing a HDT and RUT, and an oxidizing agent which is comprised of an enzyme (horseradish peroxidase) and an electron acceptor (hydrogen peroxide). The procedure is a one-step, in situ reaction, which is highly selective and which produces minimal by-products and chemical waste. The resulting copolymer solution can be immediately used as is or purified via such techniques as dialysis, centrifuging and precipitation and then used for subsequent processing strategies.

Figure 3:
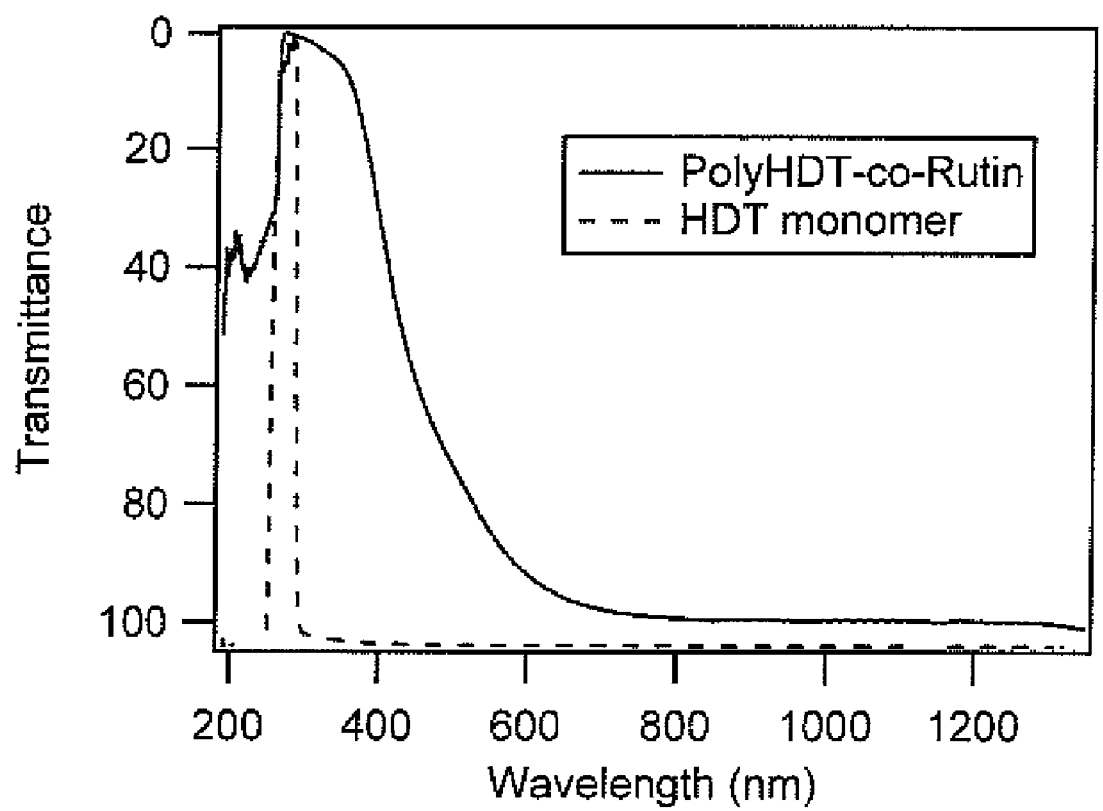
FIG. 3. UV-vis absorption spectra of the polyHDT-co-RUT formed in presence of HRP and of the monomer HDT.

FIG. 3 of this invention shows a comparison of the visible absorption spectra of the copolymerized HDT-co-RUT prepared with HRP and of the monomer HDT. As shown in this figure, strong, broad absorption well out into the visible observed for the polymerized sample. This absorption is indicative of extended conjugation found in the copolyphenol.

It is yet another objective of the present invention to provide a technique as described above which results in the synthesis of a copolyphenol where the thermal, mechanical, medical and electronic properties of the final complex can be tailored and optimized by judicious choice or modification of the monomer or co-monomers to be reacted. Possible monomers are quercitin, catechin, epicatechin, or rutin, Kaempferol, Myricetin, Delphinidin, Cyananidin, Petunidin, Pelargonidin, Malvidin, epigallocatechin gallate, flavonone, Isoflavone, Chalcone, Anthocyanidin, Chrysin, Primuletin, Fisetin, Naringin, Hesperidin, Prunin, Daidzein, Genistein, Pelargonidin, cyaniding, etc.

These monomers may include, but are not limited to, various substituent groups at the ortho and meta positions to sterically control the orientation of the monomers with respect to the polyelectrolyte matrix during the polymerization. Functional groups could include but are not limited to methoxy, methyl, ethyl, sulfonate, carboxylate and hydroxyl groups attached to the ortho or meta position of the monomer/comonomer.

The functionalities of the copolymers may be tuned to impart the required mechanical, thermal, chemical, medical, electrical and optical properties through copolymerization with other functionalized monomers. Monomers include but are not limited to quercitin, catechin, epicatechin, or rutin, Kaempferol, Myricetin, Delphinidin, Cyananidin, Petunidin, Pelargonidin, Malvidin, epigallocatechin gallate, flavonone, Isoflavone, Chalcone, Anthocyanidin, Chrysin, Primuletin, Fisetin, Naringin, Hesperidin, Prunin, Daidzein, Genistein, Pelargonidin, cyaniding, etc.

The copolymers have sites for further modifications including but not limited to covalently coupling other functionalities, thermal and UV crosslinkers and even biomolecules through simple coupling chemistry.

The copolymers will allow for use in a wide range of applications including, but not limited to, wood composites laminates, foundry resins, abrasives, friction and molding materials, coatings and adhesives, fiber bonders and flame retardants light weight rechargeable batteries, rechargeable batteries, smart windows, chaff materials, food antioxidant, drugs for various health issues such as cancer and drug delivery systems. Recently oligoepicatechin are under testing as drugs for cancer treatment. Possible monomers to be used are quercitin, catechin, epicatechin, or rutin, Kaempferol, Myricetin, Delphinidin, Cyananidin, Petunidin, Pelargonidin, Malvidin, epigallocatechin gallate, flavonone, Isoflavone, Chalcone, Anthocyanidin, Chrysin, Primuletin, Fisetin, Naringin, Hesperidin, Prunin, Daidzein, Genistein, Pelargonidin, cyaniding, etc.

The present invention is premised on the discovery that mild enzymatic synthesis can be used to prepare water soluble and processable copolymers. Improved electronic and optical properties are obtained with the approach described in this invention. In addition, with judicious choice of matrix and/or monomer, the final copolyflavonoid complex properties may be tailored to suit a wide range of industrial, electronic and optical applications.

Example 1

HDT monomer copolymerizes with QUE enzymatically in the presence of HRP activated by hydrogen peroxide to give a water soluble polyHDT-co-QUE.

Example 2

HDT monomer copolymerizes with QUE enzymatically in the presence of HRP activated by hydrogen peroxide, in a solution composed of water/ethanol (80:20).

Example 3

HDT monomer copolymerizes with QUE enzymatically in the presence of HRP activated by hydrogen peroxide, in a solution composed of water/ethanol (90:10).

Example 4

HDT monomer copolymerizes with QUE enzymatically in the presence of HRP activated by hydrogen peroxide, in a solution composed of water/ethanol (70:30).

Example 5

HDT monomer copolymerizes with QUE enzymatically in the presence of HRP activated by hydrogen peroxide, in a solution composed of water/ethanol maintained at a pH between 6.0-8.5.

Example 6

HDT monomer copolymerizes with EPI enzymatically in the presence of HRP activated by hydrogen peroxide to give a water soluble polyHDT-co-EPI.

Example 7

HDT monomer copolymerizes with EPI enzymatically in the presence of HRP activated by hydrogen peroxide, in a solution composed of water/ethanol (80:20).

Example 8

HDT monomer copolymerizes with EPI enzymatically in the presence of HRP activated by hydrogen peroxide, in a solution of water/ethanol (90:10).

Example 9

HDT monomer copolymerizes with EPI enzymatically in the presence of HRP activated by hydrogen peroxide, in a solution composed of water/ethanol (70:30).

Example 10

HDT monomer copolymerizes with EPI enzymatically in the presence of HRP activated by hydrogen peroxide, in a solution composed of water/ethanol maintained at pH between 6.0-8.5.

Example 11

HDT monomer copolymerizes with RUT enzymatically in the presence of HRP activated by hydrogen peroxide to give a water soluble polyHDT-co-RUT.

Example 12

HDT monomer copolymerizes with RUT enzymatically in the presence of HRP activated by hydrogen peroxide, in a solution composed of water/ethanol (80:20).

Example 13

HDT monomer copolymerizes with RUT enzymatically in the presence of HRP activated by hydrogen peroxide, in a solution of water/ethanol (90:10).

Example 9

HDT monomer copolymerizes with RUT enzymatically in the presence of HRP activated by hydrogen peroxide, in a solution composed of water/ethanol (70:30).

Example 10

HDT monomer copolymerizes with RUT enzymatically in the presence of HRP activated by hydrogen peroxide, in a solution composed of water/ethanol maintained at pH between 6.0-8.5.

The invention claimed is:

1. A method of producing, in situ, a copolymer of hydroxytyrosol or a derivative of hydroxytyrosol having functional groups selected from the group consisting of methoxy, methyl, ethyl, sulfonate, carboxylate and hydroxyl groups, and at least one flavonoid comprising:
reacting, in situ, hydroxytyrosol monomers or derivative of hydroxytyrosol, with at least one flavonoid in a mixed solution comprising an enzyme, hydrogen peroxide, and an aqueous solvent.

2. The method of claim 1 wherein the flavonoid is selected from the group consisting of quercitin, catechin, epicatechin, and rutin.

3. The method of claim 1 wherein the enzyme is selected from the group consisting of horse radish peroxidase, laccase and pegylated hemadine.

4. The method of claim 1 wherein the step of reacting hydroxytyrosol monomers with the flavonoid is conducted at a temperature of 5 to 37 C.

5. The method of claim 1 wherein the amount of enzyme is 0.4 to 2 mg/mL of the mixed solution.

6. The method of claim 1 wherein the amount of hydrogen peroxide is 0.1 to 3% per volume of the mixed solution.

7. The method of claim 1 wherein the pH of the mixed solution is 4.3 to 8.5.

8. The method of claim 1 wherein the pH of the mixed solution is 6.0 to 8.5.

9. The method of claim 1 wherein the aqueous solvent comprises ethanol and water.

* * * * *